United States Patent [19]
Asher et al.

[11] Patent Number: 5,728,127
[45] Date of Patent: Mar. 17, 1998

[54] APPARATUS FOR MAINTAINING VERTEBRAE OF A SPINAL COLUMN IN A DESIRED SPATIAL RELATIONSHIP

[75] Inventors: Marc A. Asher, Leawood, Kans.; Charles F. Heinig, Wareneck, Va.; Terrence M. Stahurski, Seven Hills, Ohio

[73] Assignee: Acro Med Corporation, Cleveland, Ohio

[21] Appl. No.: 495,850

[22] Filed: Jun. 27, 1995

[51] Int. Cl.$^6$ ............................................. A61B 17/70
[52] U.S. Cl. ........................ 606/61; 606/69; 606/72; 606/73; 606/75
[58] Field of Search ........................ 606/60, 61, 69, 606/70, 71, 72, 73, 75

[56] References Cited

U.S. PATENT DOCUMENTS

| | | | |
|---|---|---|---|
| 4,047,524 | 9/1977 | Hall | 606/75 |
| 4,696,290 | 9/1987 | Steffee | 606/61 |
| 4,854,311 | 8/1989 | Steffee | 606/73 |
| 5,108,395 | 4/1992 | Laurain | 606/61 |
| 5,234,431 | 8/1993 | Keller | 606/70 |
| 5,261,909 | 11/1993 | Sutterlin et al. | 606/61 |

*Primary Examiner*—Michael Buiz
*Assistant Examiner*—David O. Reip
*Attorney, Agent, or Firm*—Tarolli, Sundheim, Covell, Tummino & Szabo

[57] ABSTRACT

An apparatus for maintaining vertebrae of a spinal column in a desired spatial relationship includes a longitudinal member extendable along the spinal column. A fastener connects the longitudinal member to a vertebra. The fastener has a first end portion engaging a vertebra and a second end portion. A staple, through which the second end portion of the fastener is extendable, includes a plurality of projections for engaging a vertebra. A washer, including an opening through which the second end portion of the fastener is extendable, engages the staple and the longitudinal member. The washer prevents pivotal movement of the longitudinal member relative to the staple. The longitudinal member, the fastener, the staple, and the washer are connected together.

61 Claims, 3 Drawing Sheets

5,728,127

APPARATUS FOR MAINTAINING VERTEBRAE OF A SPINAL COLUMN IN A DESIRED SPATIAL RELATIONSHIP

BACKGROUND OF THE INVENTION

The present invention relates to an apparatus for maintaining vertebrae of a spinal column in a desired spatial relationship. More specifically, the present invention is directed to an apparatus for maintaining vertebrae of a spinal column in a desired spatial relationship to be fixed to an anterior portion of a spinal column.

U.S. Pat. No. 5,108,395 discloses a known apparatus for maintaining vertebrae of a spinal column in a desired spatial relationship that is anteriorly fixed to a spinal column. U.S. Pat. No. 5,108,395 discloses a plate extendable along a spinal column. The plate has an opening through which a tubular part of a clamp extends. A nut threadably engages the tubular part to clamp the plate to the clamp. The clamp and the plate each have radiating serrations that engage each other to position the plate in any one of a plurality of positions about an axis of the tubular part of the clamp. The clamp includes spikes that engage a vertebra. Spherical holes in the clamp receive spherical heads of screws that connect the clamp to the vertebra. The clamp may rotate relative to the screws.

SUMMARY OF THE INVENTION

In accordance with the present invention, an apparatus for maintaining vertebrae of a spinal column in a desired spatial relationship includes a longitudinal member extendable along the spinal column. A fastener including a first end portion for engaging the vertebra connects the longitudinal member to the vertebra. A second end portion of the fastener extends through an opening in a staple. The staple includes a plurality of projections for engaging the vertebra. The second end portion of the fastener extends through an opening in a washer engageable with the staple and the longitudinal member. The washer includes means for preventing pivotal movement of the longitudinal member relative to the staple. The longitudinal member, the fastener, the staple, and the washer are connected together.

The washer includes surface means defining a recess for receiving the longitudinal member. The surface means on the washer defining the recess engages the longitudinal member to prevent pivotal movement of the longitudinal member relative to the washer. The staple includes a plurality of radially extending splines engageable with radially extending splines on the washer. The splines on the washer and on the staple position the washer in any one of a plurality of positions about a longitudinal axis of the fastener and prevent relative rotation between the washer and the staple about the axis of the fastener. The staple includes surface means for engaging an intermediate portion of the fastener located between the first and second end portions of the fasteners to prevent rotation of the staple relative to the fastener. The surface means on the staple for engaging the intermediate portion of the fastener defines a recess for receiving the intermediate portion of the fastener.

BRIEF DESCRIPTION OF THE DRAWINGS

The foregoing and other features of the present invention will become apparent to one skilled in the art upon consideration of the following description of a preferred embodiment of the invention with reference to the accompanying drawings, wherein.

DESCRIPTION OF A PREFERRED EMBODIMENT OF THE INVENTION

Figure 1:
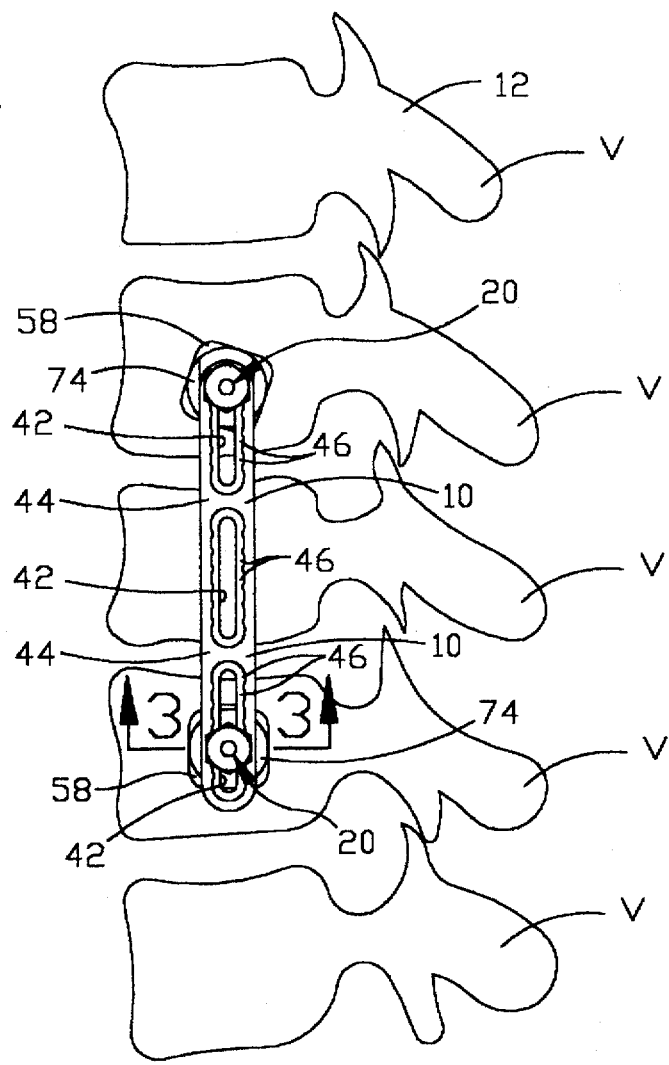
FIG. 1 is a left lateral view of a human spinal column in which an apparatus constructed in accordance with the present invention has been implanted.

A surgically implantable longitudinal plate 10 (FIG. 1) for maintaining vertebrae of a spinal column in a desired spatial relationship is connected to anterior portions of vertebrae V of a spinal column 12 by fasteners 20. The plate 10 can be contoured to conform to desired curvatures of the spinal column 12. Although the plate 10 is shown as maintaining three vertebra in a desired spatial relationship, it may be used to maintain any number of vertebrae in a desired spatial relationship.

Figure 2:
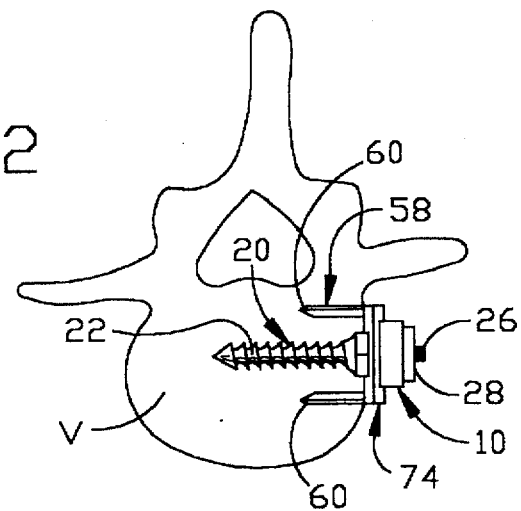
FIG. 2 is a top view of a vertebra showing the location of the apparatus in FIG. 1 on the vertebra.

The plate 10 is connected to respective vertebrae V by fasteners 20 (FIGS. 2 and 3) made of suitable biocompatible material, such as titanium or stainless steel. Each of the fasteners 20 has a threaded inner end portion 22 having a coarse helical thread convolution 24 which engages the vertebra V. An outer end portion 26 of the fastener 20 is provided with a relatively fine thread which engages an internal thread convolution on a nut 28 preferably made of a suitable biocompatible material, such as titanium or stainless steel.

Wrenching flats (not shown) are provided on the outermost end of the outer end portion 26 of the fastener 20. Torque is applied to these wrenching flats to turn the relatively coarse helical thread convolution 24 into the vertebra V. Once the fastener 20 has been connected to the vertebra and the plate 10, the outer end portion of the fastener may be cut away to minimize the overall length of the fastener.

An intermediate portion 32 (FIG. 3) is located between the inner end portion 22 and the outer end portion 26 of fastener 20. The intermediate portion 32 is provided with wrenching flats 34 which can be engaged to remove the fastener 20 from the vertebra V. Each of the wrenching flats 34 has an opposite parallel wrenching flat 34. In addition, the intermediate portion 32 of the fastener 20 has a flat outer side surface 38. When the clamp nut 28 is tightened, the plate 10 is securely gripped between the clamp nut 28 and the intermediate portion 32 of the fastener 20.

Although it is contemplated that the fastener 20 could have many different constructions, it is preferred to construct the fastener 20 in accordance with U.S. Pat. No. 4,854,311 which is assigned to the assignee of the present invention.

The plate 10 (FIG. 1) has a length which is at least sufficient to enable the plate to span at least two vertebrae V. In the embodiment of the invention illustrated in FIG. 1, the plate 10 spans three vertebrae V. Of course, the length of the plate in any particular installation will depend upon the condition to be corrected, the size of the patient's vertebrae, and the number of vertebrae V to be held in a desired spatial relationship relative to each other by the plate.

The plate 10 includes a pair of elongate slots 42 extending along a longitudinal axis of the plate. The plate 10 may have any number of slots 42 receiving fasteners 20 depending on the length of the plate. The plate 10 has an upper surface 44 (FIG. 3) provided with a plurality of frustoconical recesses 46 (FIG. 1) along the slot 42 defining a plurality of locations for receiving the fastener 20. The frustoconical recess 46 (FIG. 3) engages a frustoconical portion 50 of the nut 28 to prevent sliding movement of the plate 10 relative to the fastener 20.

Although it is contemplated that the plate 10 could have many different constructions, it is preferred to construct the plate 10 in accordance with U.S. Pat. No. 4,696,290 which is assigned to the assignee of the present invention.

Figure 3:
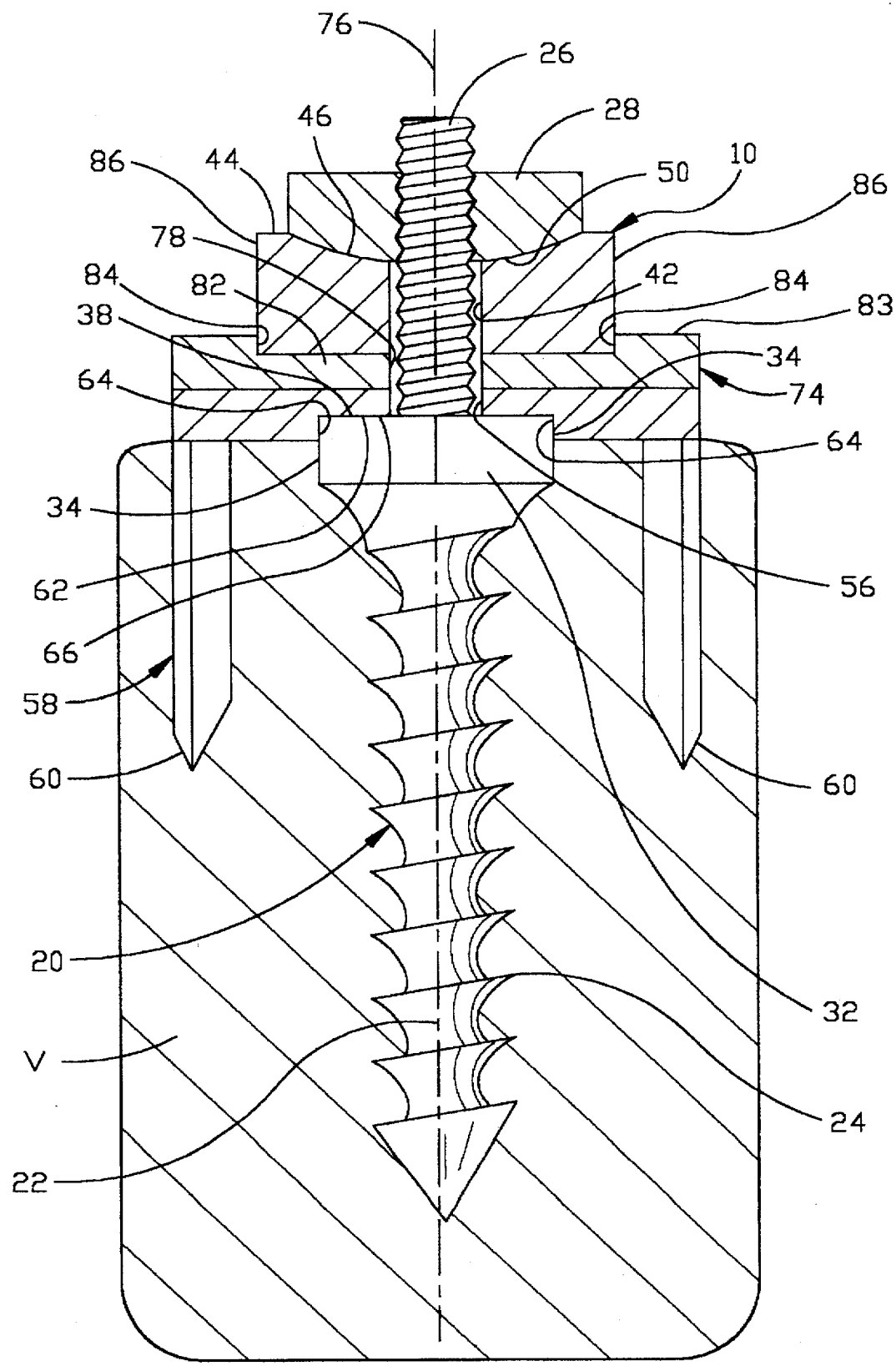
FIG. 3 is an enlarged sectional view, taken generally along the line 3—3 of FIG. 1, illustrating the manner in which a longitudinal plate is connected with a vertebra.
Figure 4:
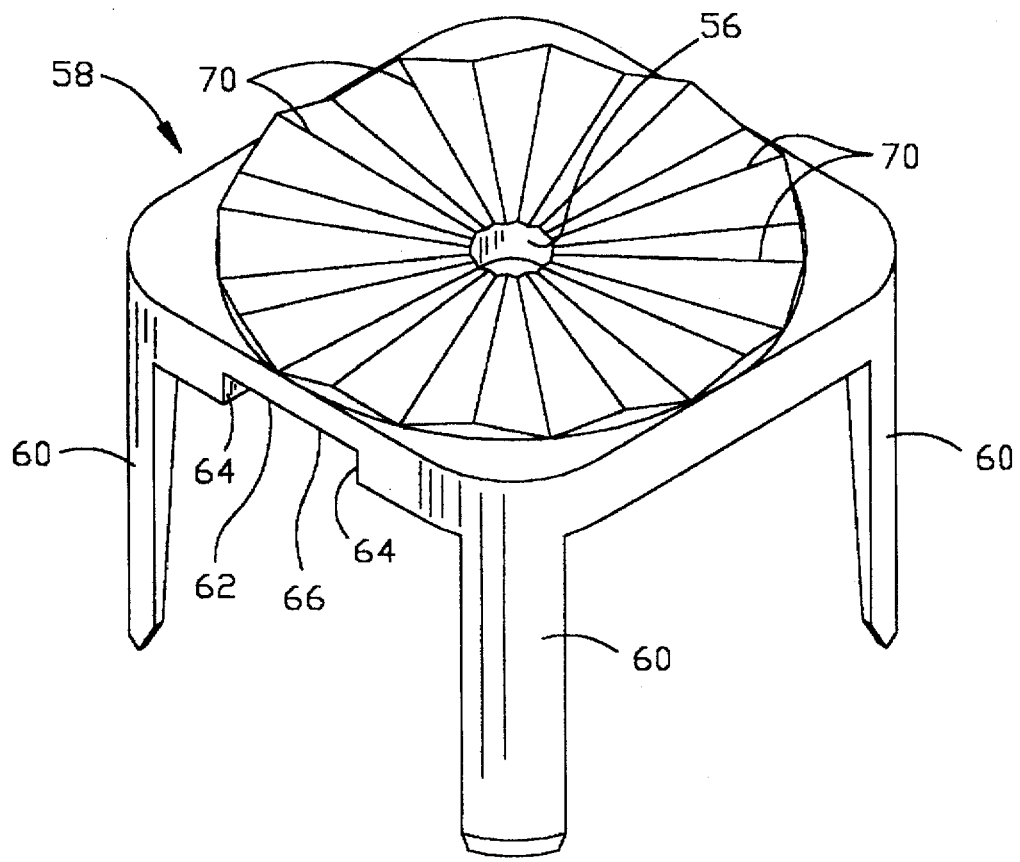
FIG. 4 is an enlarged pictorial view of a staple for use in the apparatus of FIG. 1.

The second end portion 26 of the fastener 20 extends through an opening 56 (FIGS. 3 and 4) in a staple 58 made of a suitable biocompatible material, such as stainless steel or titanium. The staple 58 includes a plurality projections 60, preferably four, for engaging the vertebra V. A recess 62 in the staple 58 receives the intermediate portion 32 of the fastener 20 (FIG. 3). Parallel side surfaces 64 define the recess 62 and engage parallel wrenching flats 34 of the intermediate portion 32 to prevent rotation of the staple relative to the fastener 20. A surface 66 (FIGS. 3 and 4) extending between the parallel side surfaces 64 of the recess 62 abuttingly engages the surface 38 of the intermediate portion 32 when the clamp nut 28 is tightened.

Figure 5:
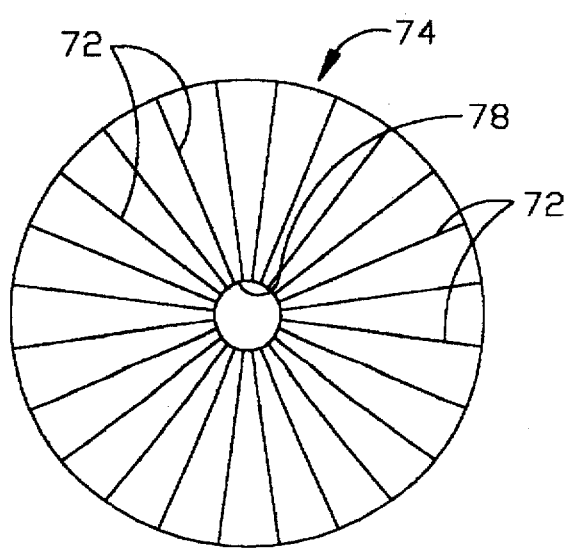
FIG. 5 is an enlarged plan view of a washer for use in the apparatus of FIG. 1.

The staple 58 includes a plurality of radially extending teeth or splines 70 (FIG. 4) for engaging matching radially extending teeth or splines 72 (FIG. 5) on a washer 74 made of a suitable biocompatible material, such as stainless steel or titanium. The splines 70 and 72 position the washer 74 in any one of a plurality of positions about a longitudinal axis 76 (FIG. 3) of the fastener 20 and prevent relative rotation between the washer and the staple 58. Although the splines 70 and 72 are shown as being triangular in shape, they may have any desired shape and be spaced from each other. Also, there may be any number of splines 70 and 72 on the staple 58 or the washer 74.

Figure 6:
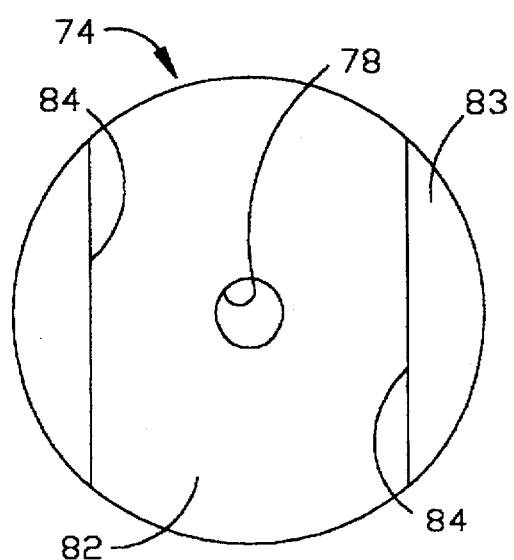
FIG. 6 is an enlarged plan view of another side of the washer of FIG. 5.

The washer includes an opening 78 (FIGS. 5 and 6) through which the second end portion 26 of the fastener extends (FIG. 3). The washer 74 (FIG. 6) includes a recess 82 in a side 83 opposite the splines 72 for receiving the plate 10. The recess 82 includes parallel side surfaces 84 (FIGS. 3 and 6) for engaging parallel side surfaces 86 (FIG. 3) on the plate 10 to prevent pivotal movement of the plate relative to the washer 84.

When the plate 10 is to be mounted on a spinal column 12, a plurality of fasteners 20 are connected to the anterior portions of vertebrae V. Staples 58 are placed over the fasteners 20 with the recesses 62 in the staples receiving the intermediate portions 32 of the fasteners. Washers 74 are then placed over the outer end portions 26 of the fasteners 20 with the radially extending splines 72 engaging the radially extending splines 70 on the staple 58. The washers 74 are positioned relative to the staples 58 and the fasteners 20 so that the recesses 82 are aligned and may receive the plate 10. After the plate 10 has been contoured to the desired configuration, if needed, the plate 10 is placed on the fasteners 20 and in the recesses 82 in the washers 74. The plate 10 can be slid along the recesses 82 in the washers 74 to position the plate relative to the washers and the staples 58 while the fasteners 20 extend through the slots 42 in the plate. The washer 74 and staple 58 connected to an upper, as viewed in FIG. 1, vertebra are in one orientation relative to the plate 10. The washer 74 and staple 58 connected to a lower, as viewed in FIG. 1, vertebra are in a second orientation relative to the plate 10.

Once the plate 10 has been positioned relative to the staples 58 and the fasteners 20, nuts 28 are threaded onto the fasteners 20 to connect the plate 10, the fastener 20, the staple 58, and the washer 74. The engagement of the intermediate portion 32 of the fastener 20 in the recess 62 in the staple 58 prevents rotation of the staple 58 relative to the fastener 20. The radially extending splines 72 engaging the radially extending splines 70 prevents rotation of the washer 74 relative to the staple 58. The engagement of the plate 10 in the recess 82 in the washer 74 prevents pivotal movement of the plate 10 relative to the washer 74. Accordingly, relative movement between the fastener 20, staple 58, washer 74, and plate 10 is prevented.

From the above description of the invention, those skilled in the art will perceive improvements, changes and modifications. Such improvements, changes and modifications within the skill of the art are intended to be covered by the appended claims.

Having described the invention, the following is claimed:

1. An apparatus for maintaining vertebrae of a spinal column in a desired spatial relationship, said apparatus comprising:

a longitudinal member extendable along the spinal column;

a fastener for connecting said longitudinal member to a vertebra including a first end portion for engaging the vertebra and a second end portion;

a staple including a plurality of projections for engaging the vertebra and an opening through which said second end portion of said fastener is extendable;

a washer having a first side engageable with said staple and a second side opposite from said first side engageable with said longitudinal member, said washer including an opening extending through said first and second sides through which said second end portion of said fastener is extendable and means for preventing pivotal movement of said longitudinal member relative to said staple; and means for connecting said longitudinal member, said fastener, said staple, and said washer together.

2. An apparatus as set forth in claim 1 wherein said means for preventing pivotal movement of said longitudinal member relative to said staple comprises surface means on said washer for engaging said longitudinal member to prevent pivotal movement of said longitudinal member relative to said washer.

3. An apparatus as set forth in claim 2 wherein said surface means on said washer defines a recess for receiving said longitudinal member.

4. An apparatus as set forth in claim 2 wherein said means for preventing pivotal movement of said longitudinal member relative to said staple further comprises a plurality of radially extending splines on said washer engageable with a plurality of radially extending splines on said staple.

5. An apparatus as set forth in claim 1 wherein said longitudinal member includes an opening through which said second end portion of said fastener is extendable.

6. An apparatus as set forth in claim 5 wherein the opening in the longitudinal member is elongate, said longitudinal member being movable relative to said washer and said staple while said second end portion of said fastener extends into the elongate opening and said longitudinal member is prevented from pivoting relative to said staple to position said longitudinal member relative to said washer.

7. An apparatus as set forth in claim 1 further including means for preventing rotation of said staple relative to said fastener.

8. An apparatus for maintaining vertebrae of a spinal column in a desired spatial relationship, said apparatus comprising:
- a longitudinal member extendable along the spinal column;
- a fastener for connecting said longitudinal member to a vertebra including a first end portion for engaging the vertebra and a second end portion;
- a staple including a plurality of projections for engaging the vertebra and an opening through which said second end portion of said fastener is extendable;
- a washer having a first side engageable with said staple and a second side opposite from said first side engageable with said longitudinal member, said washer having an opening extending through said first and second sides through which said second end portion of said fastener is extendable, said washer having a plurality of positions about a longitudinal axis of said fastener;
- means for preventing relative rotation between said washer and said staple about the longitudinal axis of said fastener when said washer is in one of said plurality of positions; and
- means for connecting said longitudinal member, said fastener, said staple, and said washer together.

9. An apparatus as set forth in claim 8 wherein said means for preventing relative rotation between said washer and said staple comprises a plurality of radially extending splines on said staple and a plurality of radially extending splines on said washer engageable with said splines on said staple.

10. An apparatus as set forth in claim 8 further including means for preventing pivotal movement of said longitudinal member relative to said washer about the axis of said fastener.

11. An apparatus as set forth in claim 10 wherein said means for preventing pivotal movement of said longitudinal member relative to said washer comprises surface means on said washer for engaging said longitudinal member.

12. An apparatus as set forth in claim 11 wherein said surface means on said washer defines a recess for receiving said longitudinal member including parallel side surfaces engageable with parallel side surfaces of said longitudinal member.

13. An apparatus as set forth in claim 8 wherein said longitudinal member includes an opening through which said second end portion of said fastener is extendable.

14. An apparatus as set forth in claim 13 wherein the opening in the longitudinal member is elongate, said longitudinal member being movable relative to said washer while said second end portion of said fastener extends into the elongate opening to position said longitudinal member relative to said washer.

15. An apparatus as set forth in claim 8 further including means for preventing rotation of said staple relative to said fastener.

16. An apparatus as set forth in claim 15 wherein said means for preventing rotation of said staple relative to said fastener comprises surface means on said staple for engaging an intermediate portion of said fastener located between said first and second end portions of said fastener.

17. An apparatus as set forth in claim 16 wherein said surface means on said staple defines a recess for receiving said intermediate portion of said fastener including side surfaces engageable with said intermediate portion of said fastener.

18. An apparatus as set forth in claim 8 wherein said means for connecting said longitudinal member, said fastener, said staple, and said washer together comprises a nut threadably engageable with said second end portion of said fastener.

19. An apparatus for maintaining vertebrae of a spinal column in a desired spatial relationship, said apparatus comprising:
- a longitudinal member extendable along the spinal column;
- a fastener for connecting said longitudinal member to a vertebra including a first end portion for engaging the vertebra and a second end portion;
- a staple including a plurality of projections for engaging the vertebra and an opening through which said second end portion of said fastener is extendable;
- a washer having a first side engageable with said staple and a second side opposite from said first side engaged with said longitudinal member, said washer having an opening extending through said first and second sides through which said second end portion of said fastener is extendable;
- means for preventing pivotal movement of said longitudinal member relative to said washer; and
- means for connecting said longitudinal member, said fastener, said staple, and said washer together.

20. An apparatus as set forth in claim 19 wherein said means for preventing pivotal movement of said longitudinal member relative to said washer comprises surface means on said washer for engaging said longitudinal member.

21. An apparatus as set forth in claim 20 wherein said surface means on said washer defines a recess for receiving said longitudinal member.

22. An apparatus as set forth in claim 19 wherein said staple includes a plurality of radially extending splines, said washer including a plurality of radially extending splines engageable with said splines on said staple to position said washer in any one of a plurality of positions about a longitudinal axis of said fastener and prevent relative movement between said staple and said washer about the axis of said fastener.

23. An apparatus as set forth in claim 19 further including means for preventing rotation of said staple relative to said fastener.

24. An apparatus for maintaining vertebrae of a spinal column in a desired spatial relationship, said apparatus comprising:
- a longitudinal member extendable along the spinal column;
- a fastener for connecting said longitudinal member to a vertebra including a first end portion for engaging the vertebra and a second end portion;
- a staple including a plurality of projections for engaging the vertebra and an opening through which said second end portion of said fastener is extendable;
- means for preventing rotation of said staple relative to said fastener;
- means for connecting said longitudinal member, said fastener, and said staple.

25. An apparatus as set forth in claim 24 wherein said means for preventing rotation of said staple relative to said fastener comprises surface means on said staple for engaging an intermediate portion of said fastener located between said first and second end portions of said fastener.

26. An apparatus as set forth in claim 24 wherein said washer includes surface means for engaging said longitudinal member to prevent pivotal movement of said longitudinal member relative to said washer.

27. An apparatus as set forth in claim 26 wherein said surface means on said washer defines a recess for receiving said longitudinal member.

28. An apparatus as set forth in claim 24 wherein said washer includes a plurality of radially extending splines, said staple including a plurality of radially extending splines engageable with said splines on said washer to position said washer in any one of a plurality of positions about a longitudinal axis of said fastener and prevent rotation of said washer relative to said staple.

29. An apparatus as set forth in claim 24 wherein said longitudinal member includes an opening through which said second end portion of said fastener is extendable.

30. An apparatus as set forth in claim 29 wherein the opening in the longitudinal member is elongate, said longitudinal member being movable relative to said washer and said staple while said second end portion of said fastener extends into the elongate opening to position said longitudinal member relative to said washer.

31. An apparatus for maintaining vertebrae in a desired spatial relationship, said apparatus comprising:

a longitudinal member extendable along the spinal column;

a fastener for connecting said longitudinal member to a vertebra including a first end portion for engaging the vertebra and a second end portion;

a staple including a plurality of projections for engaging the vertebra, an opening through which said second end portion of said fastener is extendable, and a plurality of radially extending splines;

a washer including an opening extending through a first side and a second side opposite from said first side through which said second end portion of said fastener is extendable, a plurality of radially extending splines for engaging said splines on said staple to position said washer in any one of a plurality of positions about a longitudinal axis of said fastener and to prevent relative rotation between said washer and said staple, said splines being located on said first side of said washer, and surface means for engaging said longitudinal member located on said second side of said washer to prevent pivotal movement of said longitudinal member about the axis of said fastener relative to said washer; and means for connecting said longitudinal member, said fastener, said staple, and said washer together.

32. An apparatus as set forth in claim 31 wherein said surface means for engaging said longitudinal member on said washer defines a recess for receiving said longitudinal member.

33. An apparatus as set forth in claim 32 wherein said surface means on said washer defining said recess includes parallel side surfaces engageable with parallel side surfaces of said longitudinal member.

34. An apparatus as set forth in claim 31 wherein said longitudinal member includes an elongate opening through which said second end portion of said fastener is extendable, said longitudinal member being movable relative to said washer while said second end portion of said fastener extends into the elongate opening to position said longitudinal member relative to said washer.

35. An apparatus as set forth in claim 31 further including means for preventing rotation of said staple relative to said fastener.

36. An apparatus as set forth in claim 35 wherein said means for preventing rotation of said staple relative to said fastener comprises surface means on said staple defining a recess for receiving an intermediate portion of said fastener located between said first and second end portions of said fastener including side surfaces engageable with said intermediate portion of said fastener.

37. An apparatus as set forth in claim 36 wherein said means for connecting said longitudinal member, said fastener, said staple, and said washer together comprises a nut threadably engageable with said second end portion of said fastener to clamp said longitudinal member, said washer, and said staple between said nut and said intermediate portion of said fastener.

38. An apparatus for maintaining vertebrae of a spinal column in a desired spatial relationship, said apparatus comprising:

a longitudinal member extendable along the spinal column;

a fastener for connecting said longitudinal member to a vertebra including a first end portion for engaging the vertebra and a second end portion;

a staple including a plurality of projections for engaging the vertebra and an opening through which said second end portion of said fastener is extendable;

a washer having a first side engageable with said staple and a second side opposite from said first side engageable with said longitudinal member, said washer including an opening extending through said first and second sides through which said second end portion of said fastener is extendable and means for preventing pivotal movement of said longitudinal member relative to said staple, said means for preventing pivotal movement of said longitudinal member relative to said staple comprising surface means on said washer for engaging said longitudinal member to prevent pivotal movement of said longitudinal member relative to said washer, said surface means on said washer defining a recess for receiving said longitudinal member; and means for connecting said longitudinal member, said fastener, said staple, and said washer together.

39. An apparatus as set forth in claim 38 wherein said surface means on said washer defining the recess includes parallel side surfaces engageable with parallel side surfaces of said longitudinal member.

40. An apparatus for maintaining vertebrae of a spinal column in a desired spatial relationship, said apparatus comprising:

a longitudinal member extendable along the spinal column;

a fastener for connecting said longitudinal member to a vertebra including a first end portion for engaging the vertebra and a second end portion;

a staple including a plurality of projections for engaging the vertebra and an opening through which said second end portion of said fastener is extendable;

a washer having a first side engageable with said staple and a second side opposite from said first side engageable with said longitudinal member, said washer including an opening extending through said first and second sides through which said second end portion of said fastener is extendable and means for preventing pivotal movement of said longitudinal member relative to said staple; and means for connecting said longitudinal member, said fastener, said staple, and said washer together;

said longitudinal member including an elongate opening through which said second end portion of said fastener is extendable, said longitudinal member being movable relative to said washer and said staple while said second end portion of said fastener extends into the elongate opening and said longitudinal member is prevented from pivoting relative to said staple to position said longitudinal member relative to said washer.

41. An apparatus for maintaining vertebrae of a spinal column in a desired spatial relationship, said apparatus comprising:

a longitudinal member extendable along the spinal column;

a fastener for connecting said longitudinal member to a vertebra including a first end portion for engaging the vertebra and a second end portion;

a staple including a plurality of projections for engaging the vertebra and an opening through which said second end portion of said fastener is extendable;

a washer having a first side engageable with said staple and a second side opposite from said first side engageable with said longitudinal member, said washer including an opening extending through said first and second sides through which said second end portion of said fastener is extendable and means for preventing pivotal movement of said longitudinal member relative to said staple;

means for connecting said longitudinal member, said fastener, said staple, and said washer together; and means for preventing rotation of said staple relative to said fastener.

42. An apparatus as set forth in claim 41 wherein said means for preventing rotation of said staple relative to said fastener comprises surface means on said staple for engaging an intermediate portion of said fastener located between said first and second end portions of said fastener.

43. An apparatus as set forth in claim 42 wherein said surface means on said staple defines a recess for receiving said intermediate portion of said fastener including side surfaces engageable with said intermediate portion of said fastener.

44. An apparatus as set forth in claim 43 wherein said means for connecting said longitudinal member, said fastener, said staple, and said washer together comprises a nut threadably engageable with said second end portion of said fastener to clamp said longitudinal member, said staple, and said washer between said nut and said intermediate portion of said fastener.

45. An apparatus for maintaining vertebrae of a spinal column in a desired spatial relationship, said apparatus comprising:

a longitudinal member extendable along the spinal column;

a fastener for connecting said longitudinal member to a vertebra including a first end portion for engaging the vertebra and a second end portion;

a staple including a plurality of projections for engaging the vertebra and an opening through which said second end portion of said fastener is extendable;

a washer having a first side engageable with said staple and a second side opposite from said first side engageable with said longitudinal member, said washer having an opening extending through said first and second sides through which said second end portion of said fastener is extendable, said washer having a plurality of positions about a longitudinal axis of said fastener;

means for preventing relative rotation between said washer and said staple about the longitudinal axis of said fastener when said washer is in one of said plurality of positions;

means for connecting said longitudinal member, said fastener, said staple, and said washer together; and means for preventing pivotal movement of said longitudinal member relative to said washer about the axis of said fastener, said means for preventing pivotal movement of said longitudinal member relative to said washer comprising surface means on said washer for engaging said longitudinal member, said surface means on said washer defining a recess for receiving said longitudinal member including parallel side surfaces engageable with parallel side surfaces of said longitudinal member.

46. An apparatus for maintaining vertebrae of a spinal column in a desired spatial relationship, said apparatus comprising:

a longitudinal member extendable along the spinal column;

a fastener for connecting said longitudinal member to a vertebra including a first end portion for engaging the vertebra and a second end portion;

a staple including a plurality of projections for engaging the vertebra and an opening through which said second end portion of said fastener is extendable;

a washer having a first side engageable with said staple and a second side opposite from said first side engageable with said longitudinal member, said washer having an opening extending through said first and second sides through which said second end portion of said fastener is extendable, said washer having a plurality of positions about a longitudinal axis of said fastener;

means for preventing relative rotation between said washer and said staple about the longitudinal axis of said fastener when said washer is in one of said plurality of positions; and means for connecting said longitudinal member, said fastener, said staple, and said washer together;

said longitudinal member including an elongate opening through which said second end portion of said fastener is extendable, said longitudinal member being movable relative to said washer while said second end portion of said fastener extends into the elongate opening to position said longitudinal member relative to said washer.

47. An apparatus for maintaining vertebrae of a spinal column in a desired spatial relationship, said apparatus comprising:

a longitudinal member extendable along the spinal column;

a fastener for connecting said longitudinal member to a vertebra including a first end portion for engaging the vertebra and a second end portion;

a staple including a plurality of projections for engaging the vertebra and an opening through which said second end portion of said fastener is extendable;

a washer having a first side engageable with said staple and a second side opposite from said first side engageable with said longitudinal member, said washer having an opening extending through said first and second sides through which said second end portion of said fastener is extendable, said washer having a plurality of positions about a longitudinal axis of said fastener;

means for preventing relative rotation between said washer and said staple about the longitudinal axis of said fastener when said washer is in one of said plurality of positions; and means for connecting said longitudinal member, said fastener, said staple, and said washer together, said means for connecting said longitudinal member, said fastener, said staple, and said washer together comprising a nut threadably engageable with said second end portion of said fastener.

48. An apparatus for maintaining vertebrae of a spinal column in a desired spatial relationship, said apparatus comprising:

a longitudinal member extendable along the spinal column;

a fastener for connecting said longitudinal member to a vertebra including a first end portion for engaging the vertebra and a second end portion;

a staple including a plurality of projections for engaging the vertebra and an opening through which said second end portion of said fastener is extendable;

a washer having a first side engageable with said staple and a second side opposite from said first side engageable with said longitudinal member, said washer having an opening extending through said first and second sides through which said second end portion of said fastener is extendable;

means for preventing pivotal movement of said longitudinal member relative to said washer, said means for preventing pivotal movement of said longitudinal member relative to said washer comprising surface means on said washer for engaging said longitudinal member, said surface means on said washer defining a recess for receiving said longitudinal member; and means for connecting said longitudinal member, said fastener, said staple, and said washer together.

49. An apparatus as set forth in claim 48 wherein said surface means on said washer defining said recess includes parallel side surfaces engageable with parallel side surfaces of said longitudinal member.

50. An apparatus as set forth in claim 49 wherein the opening in said washer through which said second end portion of said fastener is extendable is located in said recess.

51. An apparatus as set forth in claim 50 wherein said longitudinal member includes an opening through which said second end portion of said fastener is extendable.

52. An apparatus as set forth in claim 51 wherein the opening in said longitudinal member is elongate, said elongate opening having a longitudinal axis extending parallel to said parallel side surfaces of said longitudinal member, said longitudinal member being movable relative to said washer while said second end portion of said fastener extends into the elongate opening to position said longitudinal member relative to said washer.

53. An apparatus for maintaining vertebrae of a spinal column in a desired spatial relationship, said apparatus comprising:

a longitudinal member extendable along the spinal column;

a fastener for connecting said longitudinal member to a vertebra including a first end portion for engaging the vertebra and a second end portion;

a staple including a plurality of projections for engaging the vertebra and an opening through which said second end portion of said fastener is extendable;

a washer having a first side engageable with said staple and a second side opposite from said first side engageable with said longitudinal member, said washer having an opening extending through said first and second sides through which said second end portion of said fastener is extendable;

means for preventing pivotal movement of said longitudinal member relative to said washer;

means for connecting said longitudinal member, said fastener, said staple, and said washer together; and means for preventing rotation of said staple relative to said fastener.

54. An apparatus as set forth in claim 53 wherein said means for preventing rotation of said staple relative to said fastener comprises surface means on said staple defining a recess for receiving an intermediate portion of said fastener located between said first and second end portions of said fastener including side surfaces engageable with said intermediate portion of said fastener.

55. An apparatus for maintaining vertebrae of a spinal column in a desired spatial relationship, said apparatus comprising:

a longitudinal member extendable along the spinal column;

a fastener for connecting said longitudinal member to a vertebra including a first end portion for engaging the vertebra and a second end portion;

a staple including a plurality of projections for engaging the vertebra and an opening through which said second end portion of said fastener is extendable;

means for preventing rotation of said staple relative to said fastener, said means for preventing rotation of said staple relative to said fastener comprising surface means on said staple for engaging an intermediate portion of said fastener located between said first and second end portions of said fastener; and means for connecting said longitudinal member, said fastener, and said staple together.

56. An apparatus as set forth in claim 55 wherein said surface means on said staple defines a recess for receiving said intermediate portion of said fastener including side surfaces engageable with said intermediate portion of said fastener.

57. An apparatus as set forth in claim 56 wherein said surface means on said staple defining the recess includes parallel side surfaces engageable with parallel side surfaces of said intermediate portion.

58. An apparatus as set forth in claim 56 wherein said means for connecting said longitudinal member, said fastener, and said staple together comprises a nut threadably engageable with said second end portion of said fastener to clamp said longitudinal member and said staple between said nut and said intermediate portion of said fastener.

59. An apparatus for maintaining vertebrae of a spinal column in a desired spatial relationship, said apparatus comprising:

a longitudinal member extendable along the spinal column;

a fastener for connecting said longitudinal member to a vertebra including a first end portion for engaging the vertebra and a second end portion;

a staple including a plurality of projections for engaging the vertebra and an opening through which said second end portion of said fastener is extendable;

means for preventing rotation of said staple relative to said fastener;

means for connecting said longitudinal member, said fastener, and said staple together; and a washer engageable with said staple and said longitudinal member, said washer having an opening through which said second end portion of said fastener is extendable, said means for connecting said fastener, said longitudinal member, and said staple together including means for connecting said washer to said fastener, said longitudinal member, and said staple, said washer including surface means for engaging said longitudinal member to prevent pivotal movement of said longitudinal member relative to said washer, said surface means on said washer defining a recess for receiving said longitudinal member.

60. An apparatus as set forth in claim 59 wherein said surface means on said washer defining the recess includes parallel side surfaces engageable with parallel side surfaces of said longitudinal member.

61. An apparatus in a maintaining vertebrae of a spinal column in a desired spatial relationship, said apparatus comprising:

a longitudinal member extendable along the spinal column;

a fastener for connecting said longitudinal member to a vertebra including a first end portion for engaging the vertebra and a second end portion;

a staple including a plurality of projections for engaging the vertebra and an opening through which said second end portion of said fastener is extendable;

means for preventing rotation of said staple relative to said fastener; and means for connecting said longitudinal member, said fastener, and said staple together;

said longitudinal member including an elongate opening through which said second end portion of said fastener is extendable, said longitudinal member being movable relative to said washer and said staple while said second end portion of said fastener extends into the elongate opening to position said longitudinal member relative to said washer.

\* \* \* \* \*